(12) United States Patent
Jones et al.

(10) Patent No.: US 8,027,711 B2
(45) Date of Patent: Sep. 27, 2011

(54) LASER IMAGING APPARATUS WITH VARIABLE PATIENT POSITIONING

(75) Inventors: Sharon D. Jones, Springfield, VA (US);
Emily A. Salit, Cooper City, FL (US);
Robert H. Wake, Cooper City, FL (US);
Vincent Magraner, Miami, FL (US);
Richard A. Moya, Lake Worth, FL (US)

(73) Assignee: Imaging Diagnostic Systems, Inc., Fort Lauderdale, FL (US)

( * ) Notice: Subject to any disclaimer, the term of this patent is extended or adjusted under 35 U.S.C. 154(b) by 209 days.

(21) Appl. No.: 11/654,019

(22) Filed: Jan. 17, 2007

(65) Prior Publication Data

US 2007/0237306 A1    Oct. 11, 2007

Related U.S. Application Data

(60) Provisional application No. 60/759,066, filed on Jan. 17, 2006.

(51) Int. Cl.
*A61B 5/05* (2006.01)
(52) U.S. Cl. .............................. 600/407; 5/601; 378/37
(58) Field of Classification Search .......... 600/407–410; 5/601; 378/37
See application file for complete search history.

(56) References Cited

U.S. PATENT DOCUMENTS

| | | |
|---|---|---|
| 3,973,126 A | 8/1976 | Redington et al. |
| 3,988,793 A | 11/1976 | Abitbol |
| 4,075,883 A | 2/1978 | Glover |
| 4,485,819 A | 12/1984 | Igl |
| 4,596,384 A | 6/1986 | Blosser |
| 5,078,142 A | 1/1992 | Siczek et al. |
| 5,386,447 A | 1/1995 | Siczek |
| 5,569,266 A | 10/1996 | Siczek |
| 5,692,511 A | 12/1997 | Grable |
| 5,836,205 A * | 11/1998 | Meyer .......................... 74/89.17 |
| 5,876,339 A | 3/1999 | Lemire |
| 5,999,842 A | 12/1999 | Harrison et al. |
| 6,029,077 A * | 2/2000 | Wake et al. ................... 600/407 |
| 6,044,288 A * | 3/2000 | Wake et al. ................... 600/407 |
| 6,100,520 A * | 8/2000 | Wake et al. ................... 250/239 |
| 6,345,194 B1 * | 2/2002 | Nelson et al. ................. 600/425 |
| 6,419,390 B1 * | 7/2002 | Landis-Lowell ............. 378/209 |
| 6,480,281 B1 * | 11/2002 | Van Der Mark et al. ..... 356/432 |
| 6,769,145 B1 * | 8/2004 | Pfeuffer et al. .................. 5/601 |
| 7,034,535 B2 * | 4/2006 | Yamagata ..................... 324/318 |
| 7,254,851 B2 * | 8/2007 | Salit et al. ........................ 5/601 |
| 2002/0170116 A1 * | 11/2002 | Borders et al. .................... 5/600 |
| 2005/0055774 A1 | 3/2005 | Marin et al. |

FOREIGN PATENT DOCUMENTS

| | | |
|---|---|---|
| DE | 10026792 | 12/2001 |
| WO | WO2004/043322 | 5/2004 |
| WO | WO 2004/043535 | 5/2004 |
| WO | WO2004/096010 | 11/2004 |

* cited by examiner

*Primary Examiner* — Sanjay Cattungal
(74) *Attorney, Agent, or Firm* — Shlesinger, Arkwright & Garvey LLP

(57) ABSTRACT

A diagnostic computed tomographic imaging apparatus, comprises a patient support structure including a tabletop to support a patient in front-down, prone position. The tabletop includes an opening to permit a breast of the patient to be vertically pendant below the tabletop. A scanning mechanism is disposed below the opening and orbitable about the breast pendent through the opening to obtain perimeter data and image reconstruction data of the breast. The scanning mechanism rotates about an axis of rotation transverse to the tabletop. One of the tabletop and scanning mechanism is movable in x-y axes to center the breast about the axis of rotation.

18 Claims, 11 Drawing Sheets

LASER IMAGING APPARATUS WITH VARIABLE PATIENT POSITIONING

RELATED APPLICATION

This application claims the priority benefit of provisional application Ser. No. 60/759,066, filed Jan. 17, 2006.

FIELD OF THE INVENTION

The present invention relates to a diagnostic optical imaging apparatus that employs a near-infrared laser as a radiation source and a detector array with restricted fields of view directed to their own patches of surface of the object being scanned to simultaneously detect the intensity of light exiting from the object for the purpose of reconstructing optical cross-sectional images of that object, and particularly where the object is movable relative to the radiation source and the detector array thereby to center the object about the scanning mechanism.

BACKGROUND OF THE INVENTION

Cancer of the breast is a major cause of death among the American female population. Effective treatment of this disease is most readily accomplished following early detection of malignant tumors. Major efforts are presently underway to provide mass screening of the population for symptoms of breast tumors. Such screening efforts will require sophisticated, automated equipment to reliably accomplish the detection process.

The x-ray absorption density resolution of present photographic x-ray methods is insufficient to provide reliable early detection of malignant tumors. Research has indicated that the probability of metastasis increases sharply for breast tumors over 1 cm in size. Tumors of this size rarely produce sufficient contrast in a mammogram to be detectable. To produce detectable contrast in photographic mammograms, 2-3 cm dimensions are required. Calcium deposits used for inferential detection of tumors in conventional mammography also appear to be associated with tumors of large size. For these reasons, photographic mammography has been relatively ineffective in the detection of this condition.

Most mammographic apparatus in use today in clinics and hospitals require breast compression techniques that are uncomfortable at best and in many cases painful to the patient. In addition, x-rays constitute ionizing radiation, which adds a further risk factor into the use of mammographic techniques as most universally employed.

Ultrasound has also been suggested as in U.S. Pat. No. 4,075,883, which requires that the breast be immersed in a fluid-filled scanning chamber. U.S. Pat. No. 3,973,126 also requires that the breast be immersed in a fluid-filled chamber for an x-ray scanning technique.

In recent times, the use of light and more specifically laser light to noninvasively peer inside the body to reveal the interior structure has been investigated. This technique is called optical tomography. Rapid progress over the past decade has brought optical tomography to the brink of clinical usefulness. Optical tomography has the benefits compared to mammography of no breast compression and no ionizing radiation.

The patient lies prone on a scanning apparatus with one breast pendent in a scanning chamber. A laser beam impinges upon the breast; light is scattered throughout the breast and detected by an array of optical detectors. The scanning apparatus acquires data from one or several slices through the breast, parallel to the chest wall. The detection mechanism then moves some small distance away from the chest wall and the data for more slices are acquired. This process continues until the entire breast has been imaged.

One complication, and the subject of the present invention, is that the shape of the breast varies from patient to patient and particularly changes dramatically as the scanning proceeds from the chest wall toward the nipple. It is an absolute requirement of a $3^{rd}$ generation optical CT scanner that the center of rotation of the scanning mechanism lay within the breast. It is desirable that the center of rotation of the scanning mechanism lies near the center of the breast. But breasts do not hang vertically in the prone position. Cooper's Droop occurs when Cooper's ligaments stretch over time, causing the breasts to sag when upright. In the prone position, breasts hang somewhat towards the feet as the scanning apparatus progresses from the chest towards the nipple (see FIG. 3A). A breast that is well centered at the chest wall through the axis of rotation of the scanning mechanism usually will be off-center near the nipple.

OBJECTS AND SUMMARY OF THE INVENTION

It is an object of the present invention to provide a laser imaging apparatus that acquires photon intensity data by direct observation of the surface of a scanned object, particularly of a breast, reconstructs cross-sectional images of the optical properties of the breast, and accommodates a relatively wider range of breast shapes and therefore patients.

It is another object of the present invention to provide a laser imaging apparatus for providing reconstructed cross-sectional images of a breast from a relatively wide range of breast shapes by maintaining the center of the breast through a center of rotation of a laser scanning mechanism of the apparatus by relative motion between the patient and the scanning mechanism.

It is still another object of the present invention to provide a laser imaging apparatus for providing reconstructed cross-sectional images of a breast from a relatively wide range of breast shapes by controlling the aiming of the laser used in scanning so that the breast is constantly illuminated whether or not the breast is centered in the scanning chamber.

In summary, the present invention provides a diagnostic computed tomographic imaging apparatus, comprising a patient support structure including a tabletop to support a patient in front-down, prone position. The tabletop includes an opening to permit a breast of the patient to be vertically pendant below the tabletop. A scanning mechanism is disposed below the opening and orbitable about the breast pendent through the opening to obtain perimeter data and image reconstruction data of the breast. The scanning mechanism rotates about an axis of rotation transverse to the tabletop. One of the tabletop and scanning mechanism is movable in x-y axes to center the breast about the axis of rotation. An alternative to translating the tabletop or the scanning mechanism is to control the aiming of the laser so that the breast is illuminated at all orbital angles during scanning, independent of the position of the breast within the scanning chamber.

These and other objectives of the present invention will become apparent from the following detailed description.

DETAILED DESCRIPTION OF THE INVENTION

Figure 1:
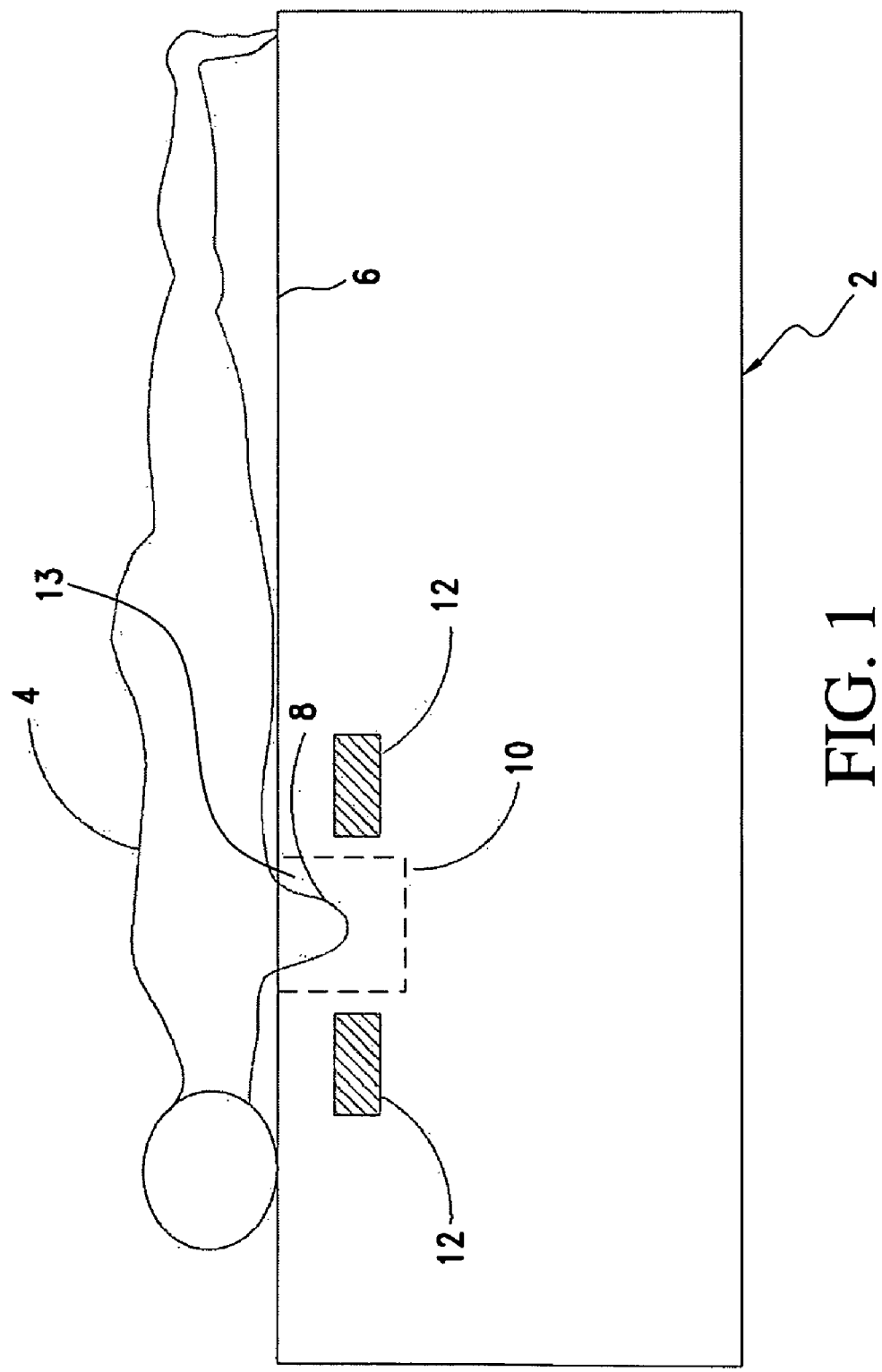
FIG. 1 is a side elevational view of an optical scanning apparatus with a detector mechanism showing a patient positioned for optical tomographic study, with one breast pendent within the scanning chamber.

Referring to FIG. 1, an optical scanning apparatus 2, as described in U.S. Pats. No. 5,692,511 and 6,100,520, supports a patient 4 on a patient support surface 6, such as a tabletop. The patient's breast 8 is pendent within a scanning chamber 10, around which orbits, revolves a detector mechanism 12. The tabletop 6 includes an opening 13 through which the breast protrudes into the scanning chamber 10. The detector mechanism 12 orbits typically 360° around the vertical axis of the scanning chamber 10 and increments vertically (the "elevator" motion) between orbits to image successive slice planes. This is repeated until all the slice planes of the object have been scanned.

Figure 2:
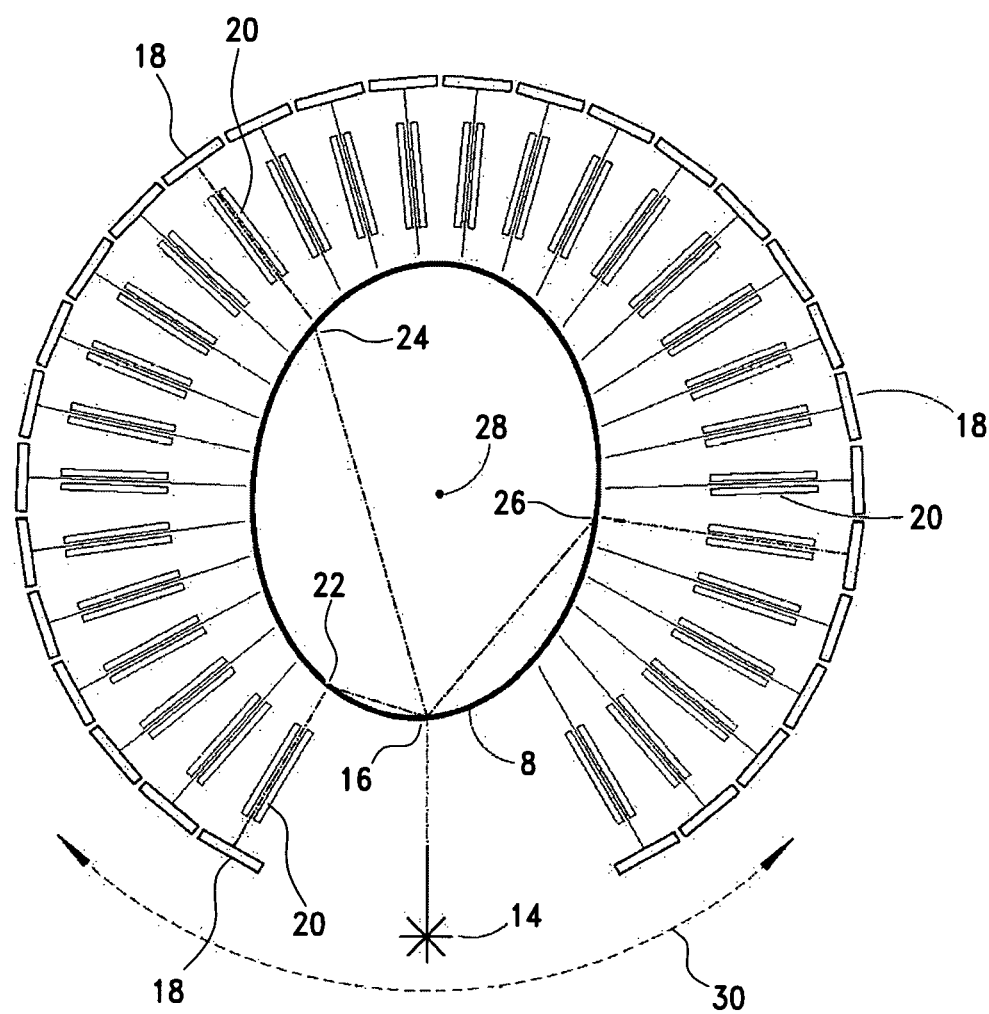
FIG. 2 is a top view of the scanning chamber of FIG. 1, showing the detector mechanism, consisting of a plurality of detectors disposed around an object being scanned and a laser light source.

FIG. 2 shows a top view of the detector mechanism 12 from FIG. 1. A laser source 14 impinges on the scanned object, such as the breast 8 at point 16. A plurality of detectors 18 define an arc surrounding the scanned object. A collimator 20 defines each detector's field of view to a small area on the surface of the scanned object. Light enters the scanned object at point 16 and exits at every point on its circumference. Three exit points, 22, 24 and 26 are shown, corresponding to three detectors. The entire mechanism rotates around the center of orbit rotation 28 as indicated by the curved arrow 30.

Every detector is preferably collimated, aiming at the center or axis of orbit rotation 28 and the laser source also points toward the center of rotation. The detectors are spaced at equal angular increments around the center of rotation. The orbit rotation is alternately 360° clockwise for one slice plane, then 360° counterclockwise for the next slice plane, as indicated by the double arrow 30.

Figure 3A:
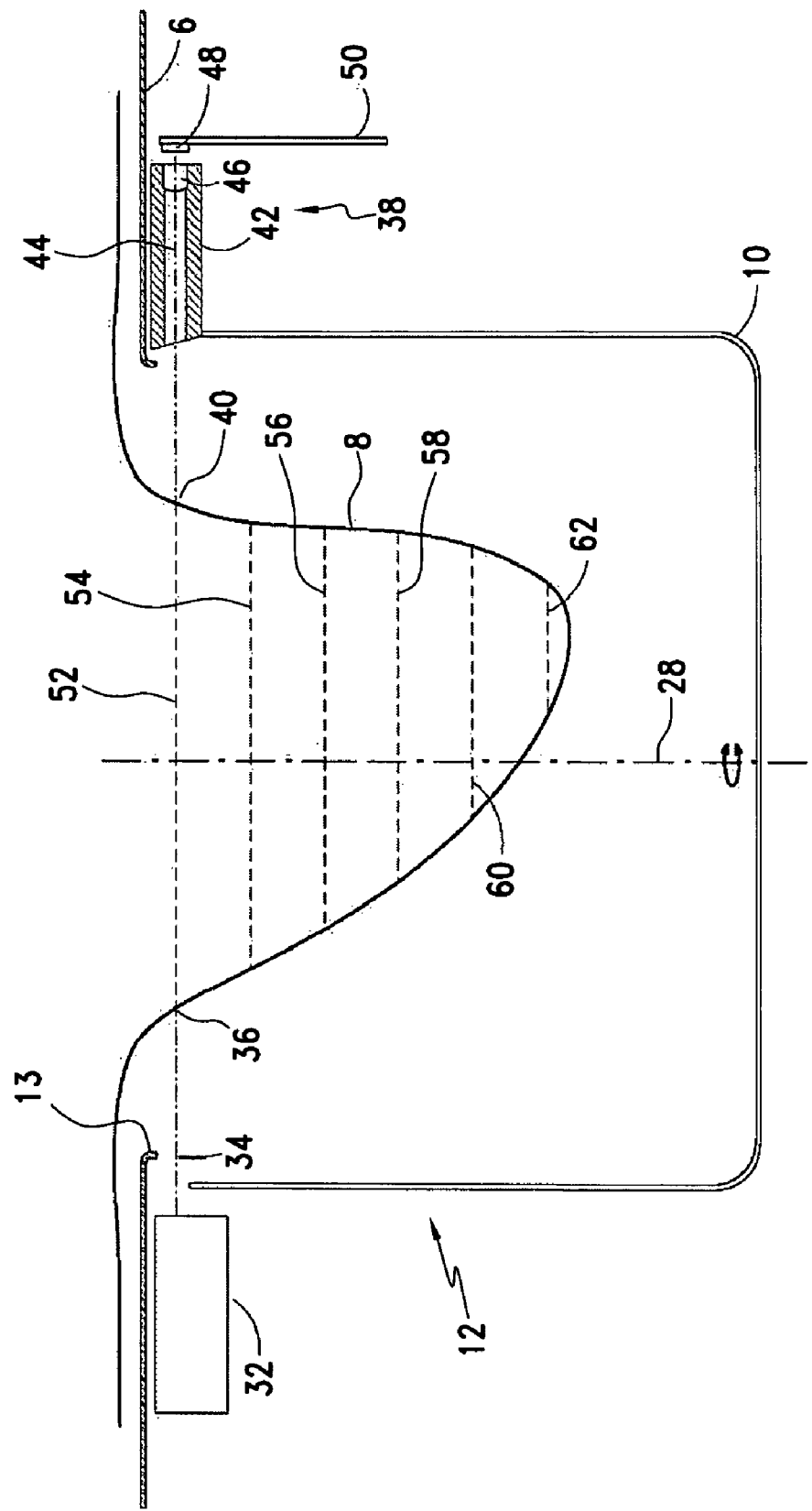
FIG. 3A is a cross-sectional view through the detector mechanism of FIG. 2, showing the breast, with pronounced Cooper's droop, being scanned, the laser light source and one detector, with the detector mechanism imaging a slice near the chest wall.

FIG. 3A shows a vertical cross-section through the detector mechanism of FIG. 2 and a patient's breast with pronounced Cooper's droop. The detector mechanism 12 is shown as imaging one slice, though any number of slices can be imaged simultaneously as disclosed in U.S. Pat. No. 6,100,520. The patient's breast 8 is pendent within the scanning chamber 10. The patient is supported by the scanning apparatus' tabletop 6. A laser 32 projects a coherent light beam 34 which impinges on the patient's breast at point 36. A detector assembly 38 is shown, imaging point 40 on the breast. Each detector assembly consists of an opaque collimator 42 with one collimating channel 44. The collimating channels can be round, square, hexagonal, triangular or another cross-sectional shape. The collimator restricts the fields of view of each detector assembly to a small, defined area on the surface of the scanned object, the breast. At the rear of each collimating channel is a lens 46, which focuses the light propagating clown the collimating channel onto the photodetector 48. The lenses are shown as plano-convex, but could be biconvex or could be eliminated if the photodetector area were larger than the collimating channel's area. The photodetectors are connected to a signal processing electronics 50, which would typically provide amplification and analog-to-digital conversion.

The laser 32 could be a semiconductor diode laser, a solid-state laser or any other near-infrared light source. The photodetectors 48 could be photodiodes, avalanche photodiodes, phototransistors, photomultiplier tubes, microchannel plates or some other photosensitive device that converts incoming light photons to an electrical signal.

Six slice planes are shown through the breast, indicated by dashed lines, though typically there will be many more, spaced at 2-4 millimeters. The scanning mechanism 12, consisting of the scanning chamber 10, the laser 32, collimators 42, detectors 48 and the signal processing electronics 50, is incremented vertically downward between slice planes. A requirement for optical tomographic imaging is that the object being scanned, the breast, surrounds the orbital rotation axis 28 at each slice plane. In other words, the breast must contain the axis of rotation at each slice plane. This condition is true for slice planes 52-60 but not for slice plane 62. At the level of slice 62, the laser beam 34 would miss the breast entirely at certain orbital angles. This would cause the acquired data at those orbital angles to be incorrect and the resultant reconstructed image would not be a faithful representation of the optical parameters of that slice of tissue.

Figure 3B:
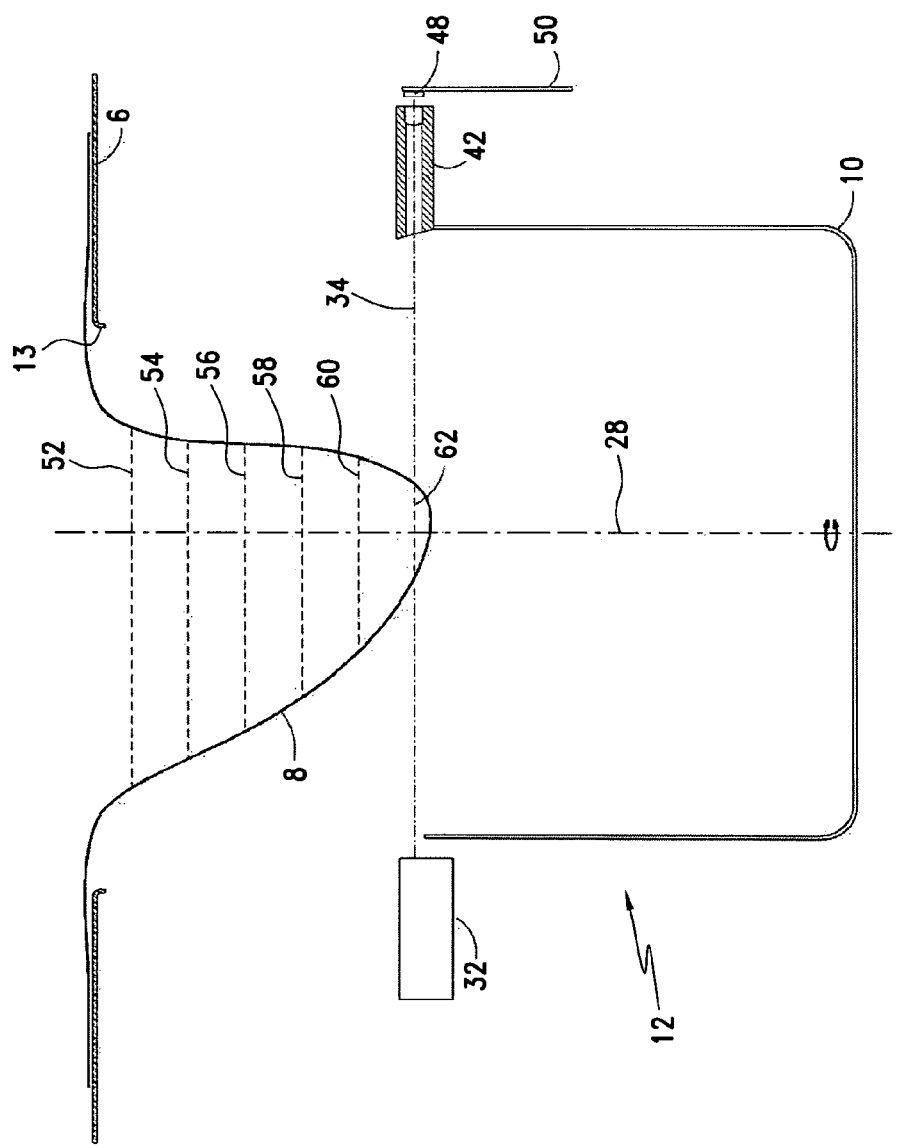
FIG. 3B is a cross-sectional view through the detector mechanism of FIG. 2, showing the breast being scanned, the laser light source and one detector, with the detector mechanism imaging a slice near the nipple and the patient and patient support having been translated with respect to the detector mechanism.

FIG. 3B shows the same vertical cross-section through the detector mechanism 12 as FIG. 3A, but with the elevator having moved the scanning mechanism to the level of slice plane 62. Additionally, the patient 4 and scanning apparatus tabletop 6 have been translated to the left with respect to the scanning mechanism, such that axis of rotation 28 is now contained within or surrounded by breast at the level of the slice plane 62. This is the essence of the present invention: permit translation between the patient and the scanning mechanism so that the breast can be repositioned to always surround or contain the orbital rotation axis 28. An alternative way of stating the same concept is to permit translation between the patient and the scanning mechanism so that the breast can be repositioned such that the laser beam always contacts the breast at all orbital angles around the breast. It is immaterial whether the patient is translated or the scanning mechanism is translated or both.

Figure 4A:
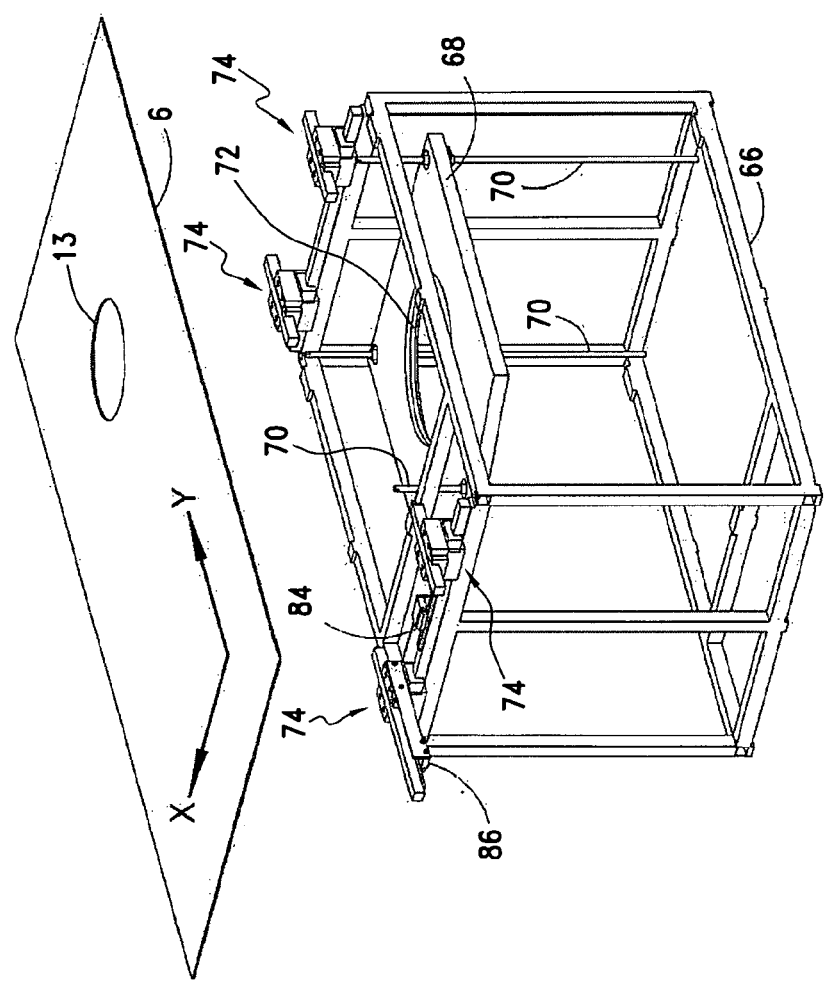
FIG. 4A is an internal structure of an optical scanning apparatus with the tabletop lifted off to show the XY tabletop translation mechanisms.

FIG. 4A shows the internal structure of an optical scanning apparatus with the tabletop 6 lifted off. A framework 66 supports the scanning mechanism and tabletop, and therefore the patient. The detector mechanism, not shown for clarity, mounts on an elevator plate 68, which moves vertically on three Acme leadscrews 70. The elevator plate 68 typically at the start the scan of a breast would be at its uppermost position, then descend in increments until the entire breast has been imaged, driven by an electric motor, not shown for clarity. The detector mechanism 12 mounts in the circular hole 72 of the elevator plate.

Figure 4B:
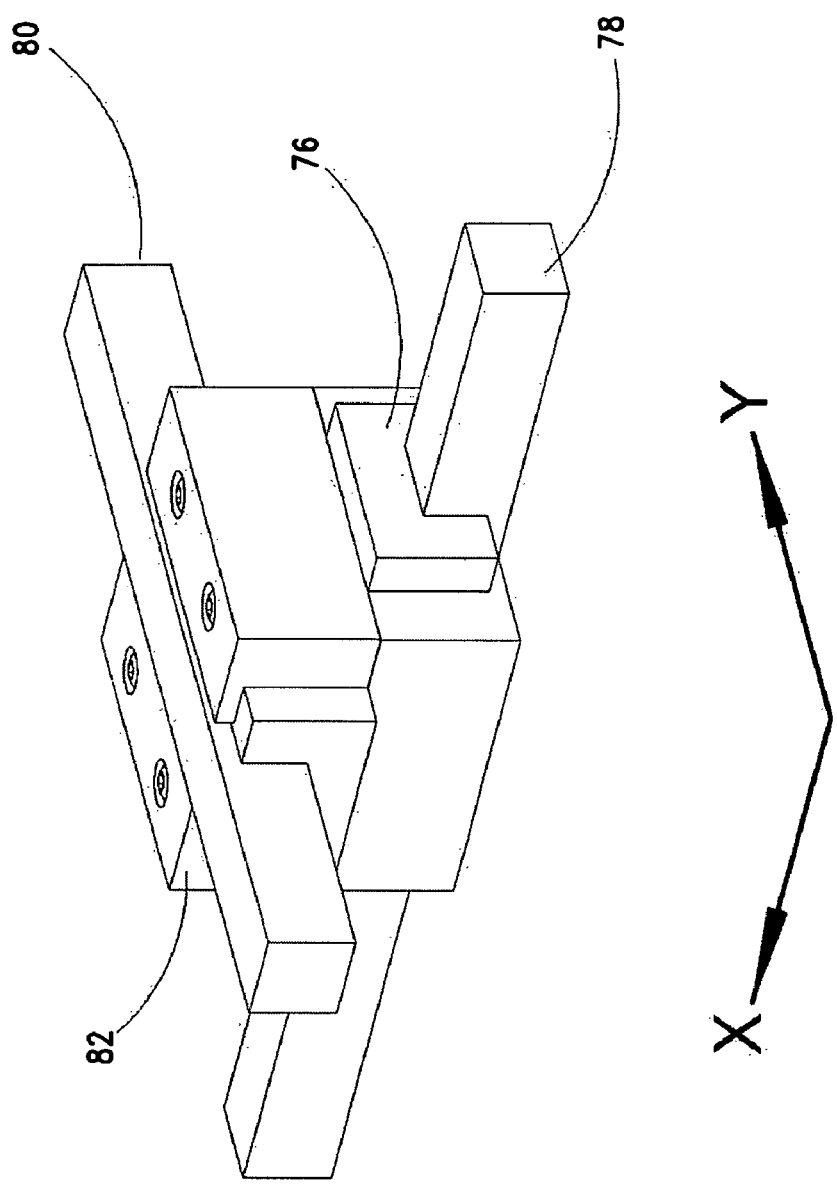
FIG. 4B is a magnified view of one of the XY tabletop translation mechanisms.

At the four corners of the framework 66 are XY translation mechanisms 74, consisting of crossed linear ball guides and rails. A magnified view of one of the XY translation mechanisms is shown in FIG. 4B. The X-axis recirculating ball guide block 76 rides on the X-axis linear rail 78, providing linear motion in the X, cross-table axis. The Y-axis linear rail 80 is mounted to the underside of the tabletop 6, shown exploded for clarity. The Y-axis recirculating ball guide block 82 provides linear motion in the Y, table-length axis and is mounted to the X-axis recirculating ball guide block 76. Four such XY translation mechanisms attach the tabletop to the framework, allowing complete XY freedom of the tabletop over a distance determined by the length of the linear rails.

Attached to the X-axis recirculating ball guide block in the upper-left corner is a X-axis linear optical encoder 84. Attached to the Y-axis recirculating ball guide block in the upper-left corner is a Y-axis linear optical encoder 86. These encoders provide the XY position of the tabletop, which information is required to locate or register the reconstructed cross-sectional images in space. This is essential for presenting 3-D representations of the breast, where all the slice images are assembled into a single volumetric image.

It should be understood that the x-axis and y-axis translation mechanisms 74 provide the means for centering the breast with the axis of rotation of the scanning mechanism.

Figure 4D:
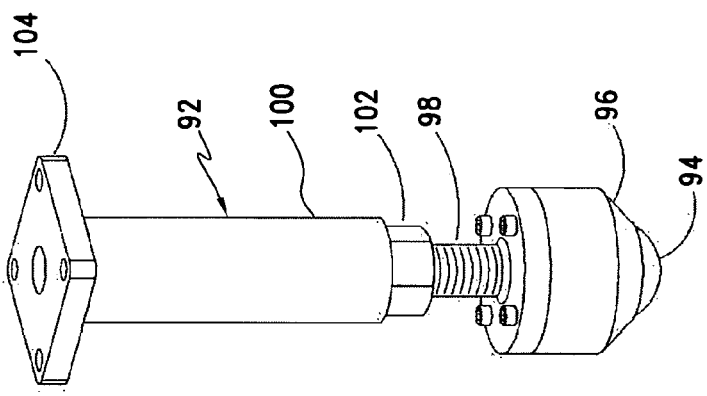
FIG. 4D is an enlarged view of the automatic centering probe of FIG. 4C.
Figure 4C:
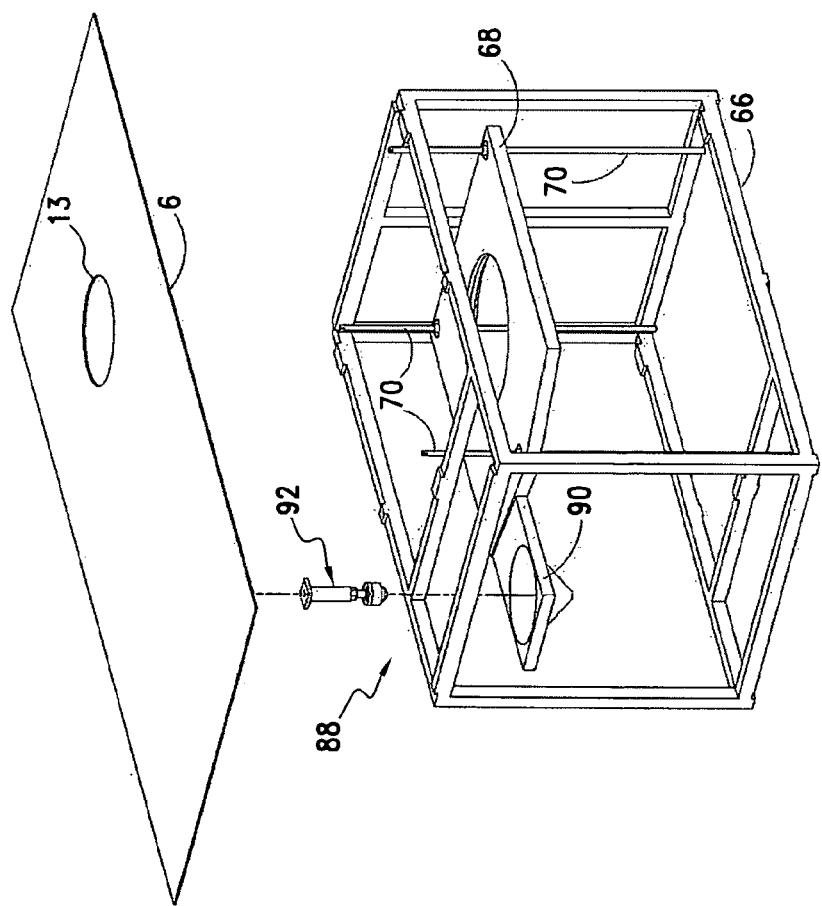
FIG. 4C is an internal structure of an optical scanning apparatus with the tabletop lifted off to show an automatic centering mechanism.

FIG. 4C shows the internal structure of an optical scanning apparatus with the tabletop 6 lifted off. The XY translation mechanisms 74 are not shown for clarity. An automatic centering mechanism 88 is shown. Before starting a scan, the scanning mechanism, mounted on the elevator plate 68, is "homed" to its uppermost position via the ACME leadscrews 70. Attached to the elevator plate is a centering cone 90 which accepts a centering probe 92. The centering probe 92 is attached to the underside of the tabletop 6. If the tabletop has been moved off its centered position (the tabletop hole 13 no longer being concentric to the scanning mechanism axis of rotation 28), the centering probe will contact the side of the centering cone and be forced to the center (bottom) of the centering cone. The centering cone is in the shape of a funnel cup, open at the top and narrows to a point at the bottom.

The centering probe assembly 92 is shown in FIG. 4D. The end of the probe is a roller ball 94, a large ball bearing, which will touch the surface of the centering cone and roll along that surface. The roller ball 94 is mounted in a polymer cup 96, machined from a low-friction plastic such as TEFLON (trademark) or RULON (trademark). The probe end is mounted on a large machine screw 98, which is threaded into a housing 100 and locked in place by a jam nut 102. The machine screw 98 and housing 100 permit adjustment of the probe length. This assembly attaches to the underside of the tabletop via a mounting flange 104.

The tabletop XY positioning is preferably a manual system, rather than motorized. An electromagnetic brake holds the tabletop in place once positioned. This brake (not shown) consists of an electromagnet, commonly used to secure emergency exit doors, attached to the framework, which bears on an iron plate attached to the tabletop. The operator releases the brake via a switch and moves the tabletop by hand to the desired position. The optical scanning apparatus acquires and displays the perimeter of the breast at each slice, as described in U.S. Pat. Nos. 6,044,288 and 6,029,077. The operator uses this perimeter information to recenter the breast in the scanning chamber.

Figures 5A, 5B:
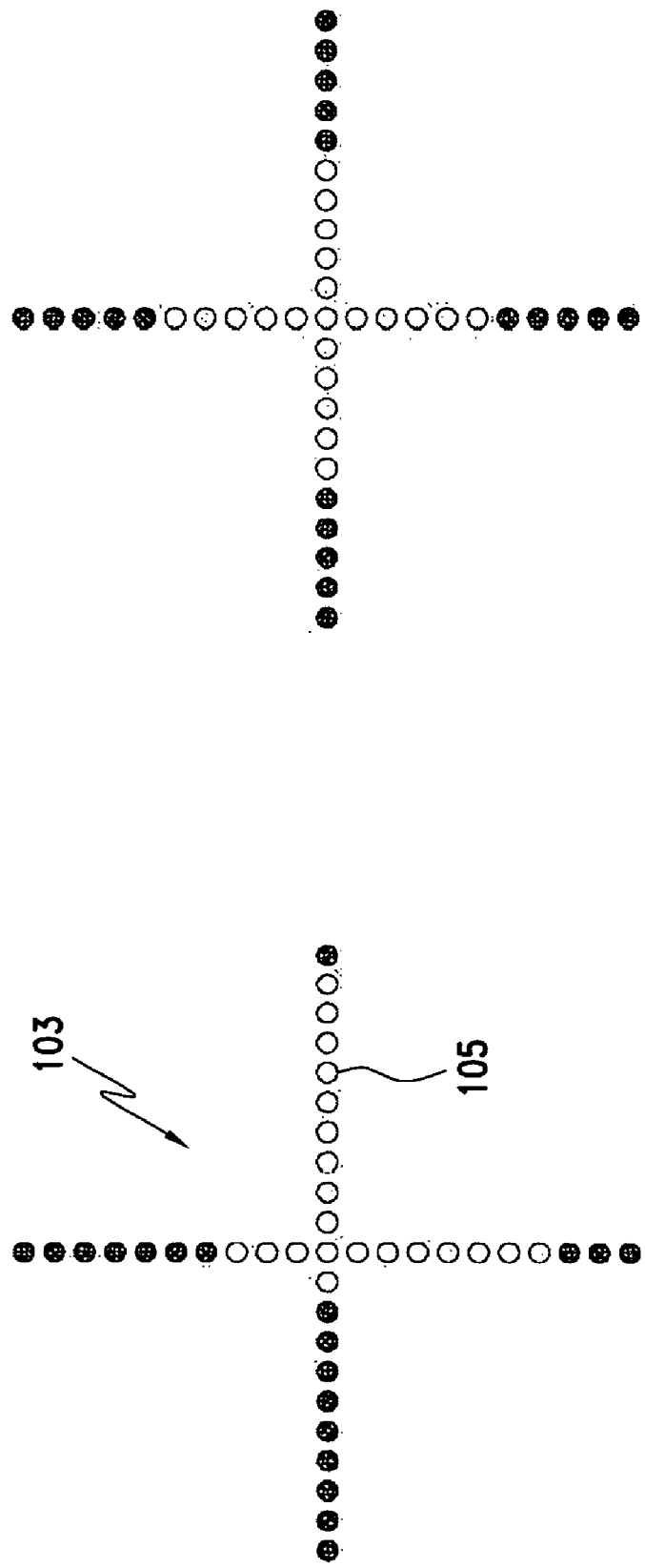
FIG. 5A shows a tabletop LED display indicating that the patient is off-center in the scanning chamber relative to the axis of rotation of the scanning mechanism.
FIG. 5B shows the tabletop LED display indicating that the patient is on-center in the scanning chamber.

FIGS. 5A and 5B illustrate an LED display 103 mounted in the tabletop that the operator uses to position the tabletop. The LED display 103 comprises two lines of individual LEDs intersecting perpendicularly into a cross, having x and y axes. The general purpose computer that controls the optical scanning apparatus will calculate the breast perimeter as described in the patents above, and illuminate the LEDs accordingly. The illuminated LEDs 105 shows the extent of off-centeredness of the breast relative to the axis of rotation. FIG. 5A indicates that the patient position is low and to the right. The operator will move the tabletop and the control computer will continuously update the LED display. The operator will move the tabletop to the left and upward until the LED pattern is as shown in FIG. 5B, where the LEDS are evenly lit about the center, indicating the breast is now centered.

The XY translation mechanisms are preferably a recirculating ball guide block riding on a linear rail. This combination provides a very low coefficient of friction, on the order of 1%. Thus the force to move the tabletop, even with a 400 lb. patient, will be on the order of 5 lbs. Many other linear positioning mechanisms could be employed, such as crossed-roller slides, polymer bushing slides, linear ball bearing slides (not recirculating) and linear tracks with rollers or cam followers.

The tabletop XY position sensors are preferably linear optical encoders, although linear potentiometers, linear variable displacement transducers (LVDTs) or rotary encoders or potentiometers attached to a windlass mechanism may also be used.

The automatic centering mechanism preferably uses a roller-ball probe entering a conical centering pocket. The centering pocket could be pyramidal, with any number of faces, or hemispherical, or virtually any other shape that is open at the top and comes to a point at the bottom.

The operator feedback for positioning preferably is an LED display in the tabletop. Any form of 2-dimensional display may also be employed to indicate the current and desired table position.

Figure 6:
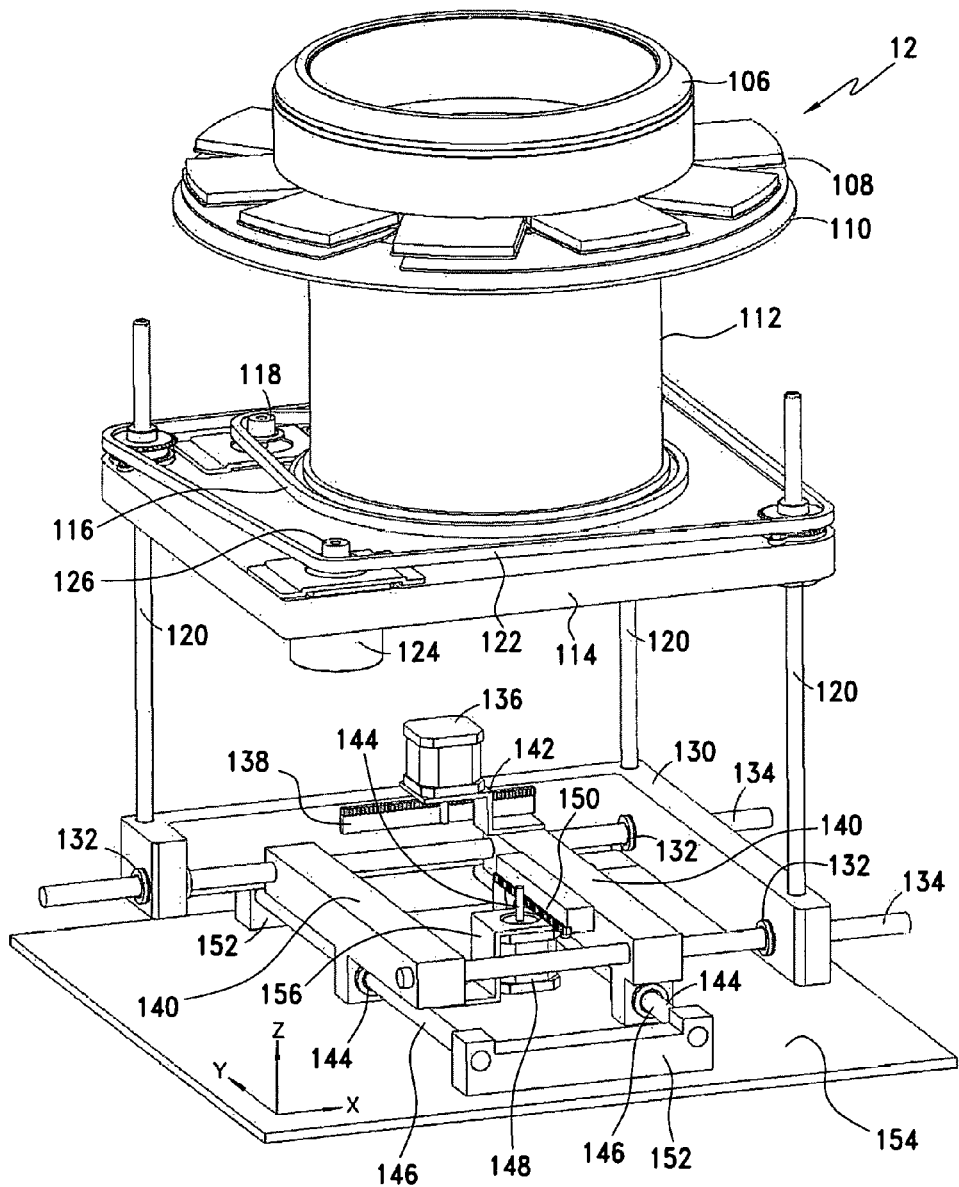
FIG. 6 shows an optical scanning mechanism with an XY translation mechanism

The embodiment of FIGS. 4A-4D discloses moving the patient on the tabletop with respect to a stationary scanning mechanism. Alternatively, the scanning mechanism could be moved with respect to a stationary tabletop and patient. FIG. 6 illustrates an optical scanning apparatus mounted on an XY translation mechanism.

In FIG. 6, collimator 106, shown with a conical mirror to fold the optical path 90°, collimates the light from the breast to detectors 108, mounted on a horizontal shelf 110. Additional disclosure of the conical mirror-collimator-detector structure is shown in WO 2004/096010. The shelf 110 is affixed to a cylindrical barrel 112 which forms the scanning chamber 10. The cylindrical barrel 112 is mounted to an elevator plate 114 via a ball bearing, which is not shown, permitting orbital rotation around its Z-axis. The scanning mechanism 12 is rotated via chain 116 and sprocket 118 by an orbit stepping motor, hidden under the elevator plate 114. The elevator plate 114 is mounted on three ACME leadscrews 120. Chain 122, driven by elevator stepping motor 124 via sprocket 126 will cause the elevator plate 114 to "crawl" up and down the ACME screws 120 via sprockets 128 (one sprocket is hidden behind the cylindrical barrel 112). With the combination of the two stepping motors, a precise helical scanning motion can be achieved. Helical scanning means that the source and detector continuously revolve around the subject while the subject is translated slowly through the plane of the source and detectors. Thus the trajectory of the detector is a helix, which is a screw thread shape.

The three ACME screws 120 are mounted on an L-shaped bracket 130 which translates in the X direction via linear bearings 132 sliding on ground rods 134. The linear bearings 132 are shown as recirculating ball bearings, though many other types of linear bearings would suffice. X-axis stepping motor 136 effects the X translation via a gear pinion, not shown for clarity, meshed with a gear rack 138. Rotation of the X-axis stepping motor 136 will cause the scanning mechanism to translate in the X direction.

The ground rods 134 are mounted on floating blocks 140, as is the X-axis stepping motor 136 via Z-bracket 142. The floating blocks 140 translate in the Y direction via linear bearings 144 sliding on ground rods 146. Y-axis stepping motor 148 effects the Y translation via a gear pinion, not shown for clarity, meshed with a gear rack 150. Rotation of the Y-axis stepping motor 148 will cause the scanning mechanism to translate in the Y direction. The Y-axis ground rods 146 are mounted on fixed blocks 152 which are mounted to a baseplate 154. The baseplate 154 also mounts the Y-axis stepping motor 148 via Z-bracket 156. The baseplate 154 is mounted to the floor of the scanner or is itself the floor of the scanner.

The optical scanning apparatus acquires and displays the perimeter of the breast at each slice, as described in U.S. Pat. Nos. 6,044,288 and 6,029,077. From this perimeter determination, the center of the breast can be determined at each slice and the controlling computer can translate the scanning mechanism in order to keep the breast centered in the scanning chamber.

The use of stepping motors for the X and Y movements advantageously obviates the need for any encoders, since the step count is exactly proportional to the position. Limit switches, not shown, are used to center the X and Y movements.

The XY translation mechanism preferably uses stepping motors for actuation and linear recirculating ball bearings sliding on ground rods for guides. DC motors, brush or brushless, rotational or linear, as actuators may also be used. Many forms of linear guide could be used as alternatives to the ground rods and ball bearings, such as the recirculating ball guides of FIG. 4B.

It should be understood that the XY translation mechanism described above provides the means for means for centering the breast with the axis of rotation of the scanning mechanism.

Figure 7:
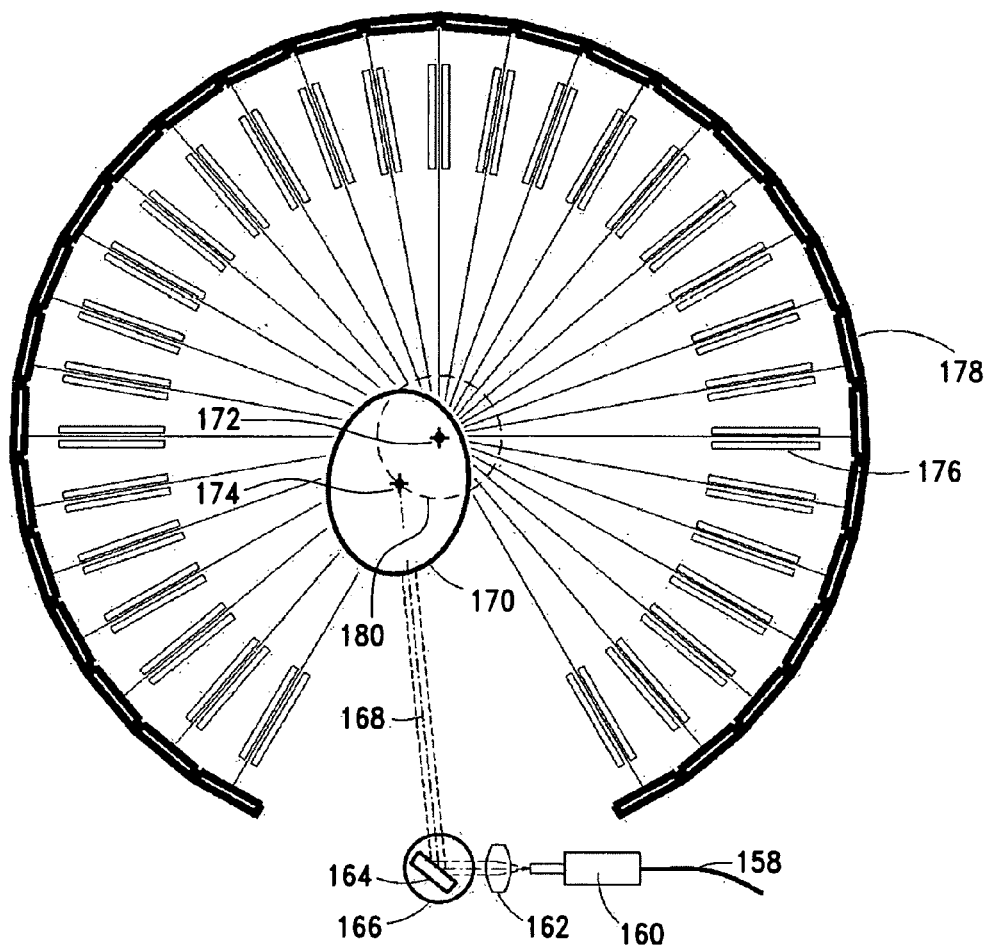
FIG. 7 shows a laser aiming apparatus in the scanning chamber of FIG. 2.
Figure 8:
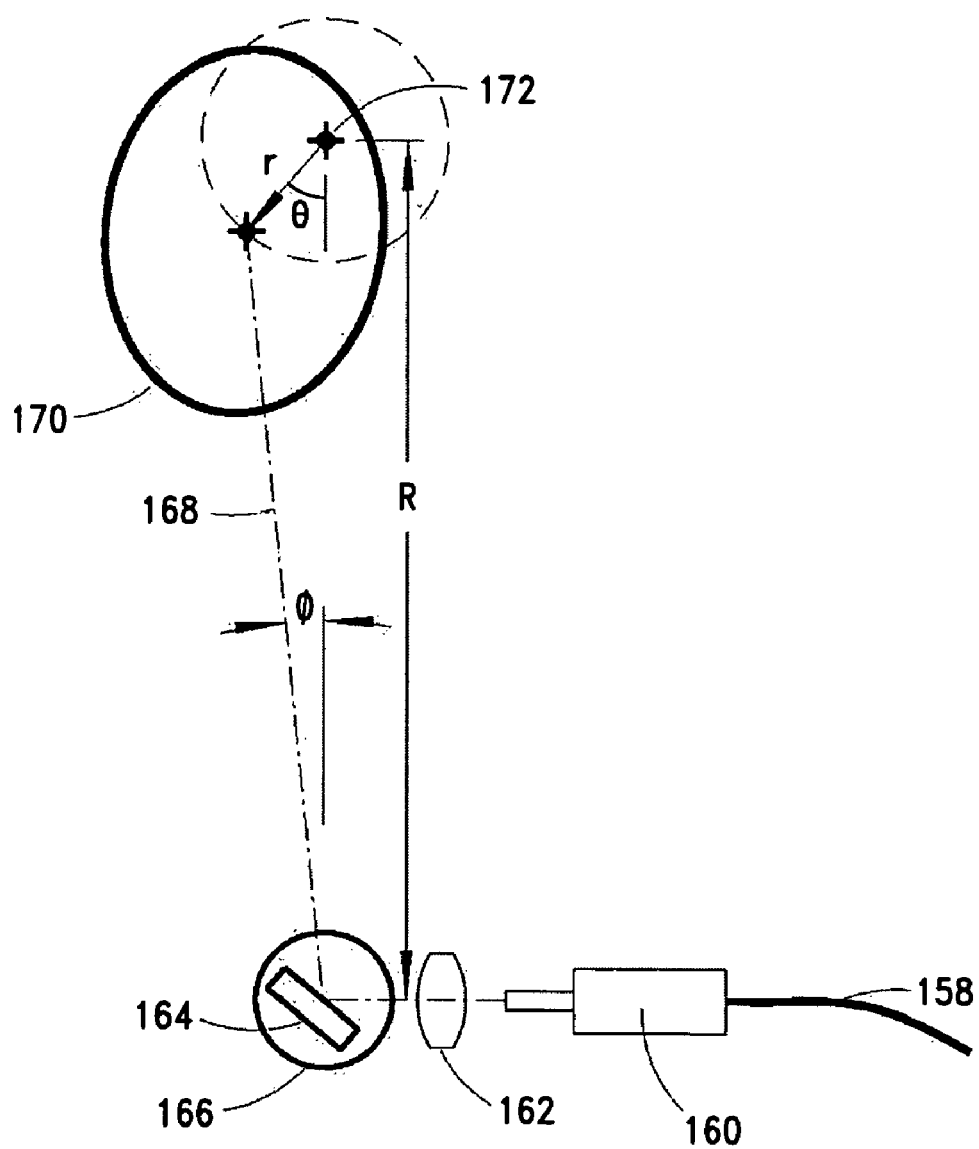
FIG. 8 shows the geometry of the laser aiming apparatus of FIG. 7.

An alternative to translating either the patient or the entire scanning mechanism is to control the aiming of the laser so that the breast is constantly illuminated, independent of its position in the scanning chamber. FIGS. 7 and 8 show a laser aiming mechanism in a scanning apparatus.

In FIG. 7, the source laser, not shown, is delivered by optical fiber 158 to an SMA connector 160. The diverging output of the SMA connector 160 is collimated into a parallel beam by lens 162. The parallel beam is directed to a turning mirror 164 which is mounted on the shaft of a galvanometer 166. The galvanometer 166 is a DC motor designed to move quickly over a small angular range, typically ±30° or less. They are commercially available from GSI Lumonics, Cambridge Technology, Nutfield Technology and others. They are designed to scan light beams in milliseconds to very high accuracy and stability over angular ranges of typically ±30°. The movement of the turning mirror 164 will deflect the laser beam 168 and control its landing spot on the breast 170. In this figure, the center of rotation of the scanning mechanism is 172 and the center of this slice of the breast is 174. The scanning mechanism consists of the laser launch mechanism 158-166, a multiplicity of collimators 176 and optical detectors 178. As the scanning mechanism rotates, the center of the breast 170 appears to describe a circle 180. The galvanometer 166 is controlled such that the laser beam 168 always points toward the center 174 of the breast 170.

The optical scanning apparatus acquires and displays the perimeter of the breast at each slice, as described in U.S. Pat. Nos. 6,044,288 and 6,029,077. From this perimeter determination, the center of the breast r can be determined. FIG. 8 shows the same view as FIG. 7, with the detector components removed for clarity. The center of the breast 170 is at a distance r and angle $\theta$ from the center of rotation 172. The distance from the turning mirror 164 to the center of rotation 108 is R. The angle of deflection $\phi$ of laser beam 168 is given by:

$$\phi = \tan^{-1}(r^* \sin(\theta)/(R - r^* \cos(\theta))) \quad \text{Equation 1}$$

The angle of deflection of the turning mirror 164 will be ½ the angle $\phi$. Equation 1 can be implemented in many ways: Computation by some general purpose computer or as a 2-dimensional lookup table, loaded in advance by a general purpose computer, indexed by r and $\theta$.

It should be understood that the turning mirror 164 along with the perimeter data of the breast provides the means for aiming the radiation source toward the center of the breast during scanning.

While this invention has been described as having a preferred design, it is understood that it is capable of further modification, uses and/or adaptations of the invention following in general the principle of the invention and including such departures from the present disclosure as come within known or customary practice in the art to which the invention pertains, and as may be applied to the essential features set forth, and fall within the scope of the invention or the limits of the appended claims.

We claim:

1. A diagnostic computed tomographic imaging apparatus, comprising:
   a) a patient support structure including a tabletop to support a patient in front-down, prone position;
   b) said tabletop including an opening to permit a breast of the patient to be vertically pendant below said tabletop;
   c) a scanning mechanism disposed below said opening and orbitable for a plurality of vertically spaced orbits around the breast pendant through said opening to obtain perimeter data and image reconstruction data of the breast, said scanning mechanism having an axis of rotation transverse to said tabletop; and
   d) one of said tabletop and scanning mechanism being movable in x-y axes to position said axis of rotation within the breast at each orbit of said scanning mechanism.

2. A diagnostic computed tomographic imaging apparatus as in claim 1, and further comprising:
   a) an electromagnetic brake to hold said tabletop in position;
   b) said brake comprising an electromagnet attached to a fixed portion of said apparatus;
   c) an iron plate attached to said tabletop; and
   d) said electromagnet when energized bearing on said iron plate to hold said tabletop in position.

3. A diagnostic computed tomographic imaging apparatus as in claim 1, wherein said opening and said axis of rotation are automatically centered to each other prior to start of scanning.

4. A diagnostic computed tomographic imaging apparatus as in claim 3, and further comprising:
  a) a threaded rod attached transversely to an underside of said tabletop, said rod having a free end;
  b) a funnel shaped cup attached to said scanning mechanism, said cup being wide at a top portion and narrow at a bottom portion;
  c) said cup being positioned to receive and engage said free end at said bottom portion when said scanning mechanism is at its topmost position; and
  d) said rod and said cup are positioned such that said opening and said axis of rotation are centered when said free end is at said bottom portion.

5. A diagnostic computed tomographic imaging apparatus as in claim 1, and further comprising:
  a) x-axis and y-axis linear guides; and
  b) said scanning mechanism is disposed on said x-axis and y-axis linear guides.

6. A diagnostic computed tomographic imaging apparatus as in claim 5, wherein said x-axis and y-axis linear guides each includes recirculating ball bearings and ground rods riding on said ball bearings.

7. A diagnostic computed tomographic imaging apparatus as in claim 1, wherein said scanning mechanism comprises an optical radiation source and a plurality of optical detectors arrayed around a scanning chamber.

8. A diagnostic computed tomographic imaging apparatus as in claim 7, wherein said optical radiation source is a near-infrared laser.

9. A diagnostic computed tomographic imaging apparatus as in claim 1, and further comprising:
  a) x-axis and y-axis linear guides; and
  b) said tabletop is disposed on said x-axis and y-axis linear guides.

10. A diagnostic computed tomographic imaging apparatus as in claim 9, wherein said x-axis and y-axis linear guides each includes a recirculating ball guide block and a linear rail riding on said guide block.

11. A diagnostic computed tomographic imaging apparatus as in claim 9, wherein said x-axis linear guide is attached to said y-axis linear guide.

12. A diagnostic computer tomographic imaging apparatus as in claim 9, and further comprising an indicator to indicate variance of said axis of rotation from the center of the breast from the perimeter data.

13. A diagnostic computed tomographic imaging apparatus as in claim as in claim 12, wherein said indicator comprises an LED display.

14. A diagnostic computed tomographic imaging apparatus as in claim 13, wherein said LED display includes a first line of individual LEDs intersecting perpendicularly to a second line of individual LEDS to form a cross.

15. A diagnostic computed tomographic imaging apparatus as in claim 14, wherein said LED display indicates centering of said axis of rotation from the center of the breast when said cross is evenly lit about its intersection.

16. A diagnostic computed tomographic imaging apparatus, comprising:
  a) a patient support structure including a tabletop to support a patient in front-down, prone position;
  b) said tabletop including an opening to permit a breast of the patient to be vertically pendant below said tabletop;
  c) a scanning mechanism disposed below said opening and orbitable for a plurality of vertically spaced orbits around the breast pendent through said opening to obtain data for image reconstruction of the breast, said scanning mechanism having an axis of rotation transverse to said tabletop; and
  d) means for positioning said axis of rotation within the breast at each orbit of said scanning mechanism.

17. A diagnostic computed tomographic imaging apparatus as in claim 16, and further comprising means for centering said axis of rotation with said opening when said scanning mechanism is at its topmost position.

18. A diagnostic computed tomographic imaging apparatus, comprising:
  a) a patient support structure including a tabletop to support a patient in front-down, prone position;
  b) said tabletop including an opening to permit a breast of the patient to be vertically pendant below said tabletop;
  c) a scanning mechanism disposed below said opening and orbitable for a plurality of vertically spaced orbits around the breast pendent through said opening to obtain data for image reconstruction of the breast, said scanning mechanism having an axis of rotation transverse to said tabletop; and
  d) said scanning mechanism including a source of radiation directed toward the breast and means for aiming said source of radiation toward the center of the breast at each orbit of said scanning mechanism.

* * * * *